(12) United States Patent
Baba et al.

(10) Patent No.: US 8,067,018 B2
(45) Date of Patent: Nov. 29, 2011

(54) MICROENCAPSULATED PYRETHRIN

(75) Inventors: Yosuke Baba, Amagasaki (JP);
Hidenori Eguchi, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1260 days.

(21) Appl. No.: 11/675,789

(22) Filed: Feb. 16, 2007

(65) Prior Publication Data

US 2007/0196411 A1    Aug. 23, 2007

(30) Foreign Application Priority Data

Feb. 21, 2006    (JP) ................................ 2006-043499

(51) Int. Cl.
*A01N 25/28* (2006.01)
*A01N 25/32* (2006.01)
*A01N 53/02* (2006.01)

(52) U.S. Cl. ........ 424/408; 424/406; 424/417; 424/418; 424/420; 424/421; 424/764; 514/65; 514/531

(58) Field of Classification Search ........................ None
See application file for complete search history.

(56) References Cited

U.S. PATENT DOCUMENTS

| | | | |
|---|---|---|---|
| 2,800,457 A | 7/1957 | Green et al. | |
| 5,292,533 A | 3/1994 | McMahon et al. | |
| 5,540,927 A | 7/1996 | Jason et al. | |
| 5,686,385 A | 11/1997 | Akashi et al. | |

FOREIGN PATENT DOCUMENTS

| | | |
|---|---|---|
| JP | 5-201821 A | 8/1993 |
| JP | 6-312904 A | 11/1994 |
| JP | 8-71406 A | 3/1996 |
| JP | 2002-114605 A | 4/2002 |

*Primary Examiner* — Neil Levy
(74) *Attorney, Agent, or Firm* — Sughrue Mion, PLLC

(57) ABSTRACT

A microcapsule comprising a core material containing pyrethrin and a capsule shell wall which surrounds said core material, said shell wall material comprises gelatin and at least one polysaccharide selected from the group consisting of gum arabic and pectin is effective for controlling insects.

3 Claims, No Drawings

MICROENCAPSULATED PYRETHRIN

FIELD OF THE INVENTION

The present invention relates to a microencapsulated pyrethrin.

BACKGROUND ART

It is well known that a microencapsulated insecticidal composition is used for controlling various insects. Further, it is also known that gelatin, biodegradable material, can be used as a wall of microcapsules in U.S. Pat. No. 5,292,533 and U.S. Pat. No. 5,540,927.

SUMMARY OF THE INVENTION

The present invention provides a microencapsulated pyrethrin. In particular, the invention provides a microcapsule comprising a core material containing pyrethrin and a capsule shell wall which surrounds said core material, said shell wall material comprises gelatin and at least one polysaccharide selected from the group consisting of gum arabic and pectin.

DISCLOSURE OF THE INVENTION

In the present invention, pyrethrin means pyrethrin I, pyrethrin II, cinerin I, cinerin II, jasmolin I, jasmolin II or mixtures thereof Natural pyrethrins, which contain the above-mentioned six insecticidal compounds, are usually available, but the pyrethrin obtained by organic synthesis may be used.

Pyrethrin is microencapsulated in the present invention. The microcapsule may contain pyrethrin solely as well as a solution of pyrethrin in the wall. Examples of the solvent used for the solution include plant oils such as corn oil, cottonseed oil, rapeseed oil and sesame oil; esters such as ethyl acetate, methyl benzoate, dimethyl phthalate and dimethyl adipate; aromatic hydrocarbons such as toluene, xylene and methylnaphthalene; aliphatic and alicyclic hydrocarbons such as hexane, cyclohexane, paraffin, kerosene and gas oil; and halogenated hydrocarbon such as chloroform and methylene chloride. The solvent may be a mixture of two or more kinds of the organic solvents mentioned above. Plant oils are preferably used because of its biodegradability. The amount of the solvent is usually 20 to 99% by weight of the pyrethrin solution. Further, powdery solid substances may be added for keeping stability of pyrethrin solution. Examples of the solid substances include natural minerals such as clay, talc, kaolin, montmorillonite, bentonite, tarra alba and silica; metal oxides such as iron oxide, copper oxide, aluminum oxide, zinc oxide, silicon oxide and titanium oxide; and salts such as calcium carbonate, magnesium carbonate, aluminum silicate, calcium sulfate and zeolite. Among them, clay, talc, amorphous silicon oxide and zinc oxide are preferably used. The average diameter (a median diameter at 50% cumulative volume) of the powdery solid substances is usually 0.05 to 50 µm and can be measured with particle distribution by laser diffraction, for example SALD-2000 (manufactured by Shimadzu Corporation). The amount of the solid substance is usually 0.1 to 30 parts by weight per 100 parts by weight of the liquid phase of the pyrethrin solution. Furthermore, auxiliaries such as synergist such as piperonyl butoxide, thickner, preservative, stabilizer, antioxidant, chelating agent, antirusting agent, antifoaming agent, pH adjusting agent and so on may be added to the pyrethrin solution.

The capsule shell wall material comprises gelatin and at least one polysaccharide selected from the group consisting of gum arabic and pectin. The amount of the gelatin is usually 20 to 100% by weight and the amount of the gum arabic and/or pectin is usually 10 to 80% by weight of the capsule shell wall material.

The capsule shell wall material can further one or more of the other polysaccharides such as xanthan gum, guar gum, carrageenan and locust bean gum. However, the capsule shell wall material preferably consists essentially of gelatin and gum arabic and/or pectin.

The average particle diameter (a median diameter at 50% cumulative volume) of the microcapsule is usually 5 to 100 µm and it can be measured with particle distribution by laser diffraction, for example SALD-2000 (manufactured by Shimadzu Corporation). The amount of the pyrethrin is usually 1 to 50%, preferably 3 to 15% by weight of the microcapsule.

The microcapsule of the present invention can be prepared by the following procedure.

Gelatin and gum arabic and/or pectin are mixed or dissolved in alkali water (e.g. aqueous sodium hydroxide) at 30-70° C. Then, pyrethrin or its solution is added under pH 5 or more and kept at 30-70° C. The pH of the mixture is adjusted to less than 5 by adding acid (e.g. aqueous acetic acid solution) and cooled with ice-water. After that, the mixture is warmed to 30-70° C. again and a hardening (e.g. calcium chloride) is added.

The amount of the capsule shell wall, wall thickness and capsule diameter can be controlled by adjusting the amount of gelatin, gum arabic or pectin; the amount of the hardening; the speed or time of stirring; or the pH value.

The capsule diameter (volume median diameter) is generally 5 µm to 100 µm. The diameter can be measured by laser diffraction SALD-2000 (manufactured by Shimadzu Corporation).

The above-mentioned procedure gives an aqueous suspension of the microcapsule of the present invention. The microcapsule can be separated from the aqueous suspension by a conventional method, but it is beneficial to utilize the aqueous suspension as it is. Further, a thickner (e.g. silicate), preservative, stabilizer, antioxidant, chelating agent, anti-rusting agent, antifoaming agent, pH adjusting agent and so on may be added for stabilizing the aqueous suspension.

The microcapsule of the present invention is used for controlling insects, typically wood harmful insects such as termites, insanitary insects such as cockroaches, unpleasant insects such as ants and agriculturally harmful insects.

Examples of the target pests include Isopteran insects such as *Coptotermes formosanus* (Formosan subterranean termite), *Reticulitermes speratus* and *Incisitermes minor*; Dictyopteran insects such as *Blattella germanica* (German cockroach), *Periplaneta fuliginosa* (smoky brown cockroach) and *Periplaneta americana* (American cockroach); Coleopteran insects such as *Lyctus brunneus* (powder post beetle), *Lasioderma serricorne* (cigarette beetle), *Dermestidae* (hide beetles) and *Scarabaeidae* (scarabs); Lepidopteran insects such as *Mamestra brassicae* (cabbage armyworm), *Pieris rapae crucivora* (common cabbageworm), *Spodoptera litura* (tobacco cutworm) and *Helicoverpa armigera* (tobacco budworm); Hymnenopteran insects such as *Camponotus japonicus*, *Pristomyrmex pungens* and *Athalia rosae ruficornis* (cabbage sawfly), Orthopteran insects such as *Oxya yezoensis* (rice grasshopper) and *Gryllidae* (crickets); Hemipteran insects; Dipteran insects; and other insects.

When the microcapsule of the present invention is used for controlling insects, the application amount is usually 0.1 to 100 g/m$^2$ in the amount of pyrethrin.

When the microcapsule of the present invention is used for controlling termites, the microcapsule is applied to a soil or concrete surface under a house in the dosage of 0.1 to 100 g/m$^2$, preferably 1 to 10 g/m$^2$, in the amount of pyrethrin, after diluting with water if necessary. The microcapsule is also applied to wood in the dosage of 0.1 to 10 g/m$^2$ in the amount of pyrethrin, after diluting with water if necessary.

When the microcapsule of the present invention is used for controlling cockroaches, the microcapsule is applied to a floor or the like where cockroaches inhabit, after diluting with water if necessary. It is preferable to apply 0.1 to 100 g/m$^2$ in the amount of pyrethrin and 10 to 1000 ml/m$^2$ of application diluent.

When the microcapsule of the present invention is used for controlling agricultural insects, the microcapsule is applied to the crops or the like where the insects inhabit, after diluting with water if necessary. It is preferable to apply 100 to 10000 liters/hectare in the amount of the application diluent.

EXAMPLES

The present invention is explained in more detail by the following examples.

Example 1

An aqueous phase was prepared by dissolving 2.8 g of gelatin originated from cattle (produced by Nitta Gelatin Inc.), 1.4 g of gum arabic (produced by Sanei Yakuhin Boeki Co.), 2-8g of pectin (produced by Wako Pure Chemical Industries) and 15 g of 0.4% aqueous sodium hydroxide solution in 105 g of ion-exchange water under heating with hot water bath. The aqueous phase was stirred at 4000 rpm with T. K. Homomixer (produced by Tokusyukikakogyo Co.) and dispersed while 80 g of 50% natural pyrethrins solution in corn oil were added thereto, and the aqueous phase was continuously stirred for 15 minutes under heating. Then, the aqueous phase was stirred at 500 rpm while 10 ml of 5% acetic acid were added to make the pH value 4.2 or less. After that, it was cooled with ice-water and stirred at 700 rpm for 30 minutes. Then, it was warmed to 30° C. and stirred at 500 rpm for 30 minutes, and 74 g of 1% aqueous calcium chloride solution were added under stirring. To make the concentration of the natural pyrethrins 10%, 0.2% aqueous Kelzan S (xanthan gum produced by Sansho Co.) solution was added to give a microcapsule formulation. The average particle diameter was measured by laser diffraction SALD-2000 (manufactured by Shimadzu Corporation) and the result of 10 μm was obtained.

Example 2

An aqueous phase was prepared by dissolving 2.8 g of gelatin originated from pig (produced by Nitta Gelatin Inc.), 1.4 g of gum arabic (produced by Sanei Yakuhin Boeki Co.), 2.8 g of pectin (produced by Wako Pure Chemical Industries) and 15 g of 0.4% aqueous sodium hydroxide solution in 105 g of ion-exchange water under heating with hot water bath. The aqueous phase was stirred at 4500 rpm with T. K. Homomixer (produced by Tokusyukikakogyo Co.) and dispersed while 80 g of 50% natural pyrethrins solution in corn oil were added thereto, and the aqueous phase was continuously stirred for 15 minutes at under heating. Then, the aqueous phase was stirred at 500 rpm while 10 ml of 5% acetic acid were added to make the pH value 4.2 or less. After that, it was cooled with ice-water and stirred at 700 rpm for 30 minutes. Then, it was warmed to 30° C. and stirred at 500 rpm for 30 minutes, and 74 g of 1% aqueous calcium chloride solution were added under stirring. To make the concentration of the natural pyrethrins 10%, 0.2% aqueous Kelzan S (xanthan gum produced by Sansho Co.) solution was added to give a microcapsule formulation. The average particle diameter was measured by laser diffraction SALD-2000 (manufactured by Shimadzu Corporation) and the result of 13 μm was obtained.

Example 3

An oil phase was prepared by mixing 80 g of PYROCIDE-50 (50% natural pyrethrins produced by McLaughlin Gormley King Co.) and 5 g of talc (average particle diameter 3 μm, Fuji Talc Industries Co.). An aqueous phase was prepared by dissolving 2.8 g of gelatin originated from pig (produced by Nitta Gelatin Inc.), 1.4 g of gum arabic (produced by Sanei Yakuhin Boeki Co.), 2.8 g of pectin (produced by Wako Pure Chemical Indusries) and 15 g of 0.4% aqueous sodium hydroxide solution in 105 g of ion-exchange water under heating with hot water bath. The aqueous phase was stirred at 5000 rpm with T. K. Homomixer (produced by Tokusyukikakogyo Co.) and dispersed while the oil phase was added thereto, and the aqueous phase was continuously stirred for 15 minutes under heating. Then, the aqueous phase was stirred at 500 rpm while 10 ml of 5% acetic acid were added to make the pH value 4.2 or less. After that, it was cooled with ice-water and stirred at 700 rpm for 30 minutes. Then, it was warmed to 30° C. and stirred at 500 rpm for 30 minutes, and 74 g of 1% aqueous calcium chloride solution were added under stirring. To make the concentration of the natural pyrethrin 10%, 0.2% aqueous Kelzan S (xanthan gum produced by Sansho Co.) solution was added to give a microcapsule formulation. The average particle diameter was measured by laser diffraction SALD-2000 (manufactured by Shimadzu Corporation) and the result of 14 μm was obtained.

This microcapsule formulation was diluted with water 100 times. After one day, float or precipitation was not found and the dilution stability was good.

Reference Example 1

Twenty grams (20 g) of PYROCIDE-50 (50% natural pyrethrins, McLaughlin Gormley King Co.), 15 g of New Kalgen CP-120 (surfactant, Takemotoyushi Co.) and 75 g of IP Solvent (hydrocarbon, Idemitsu Petrochemical Co.) were mixed to give an emulsifiable concentrate.

Test Example 1

Twenty grams (20 g) of sand were put on a plastic Petri dish (9 cm in diameter). Each formulation obtained in Examples 1-2 and Reference example 1 was diluted with ion-exchange water to a designated concentration, and 5 ml of the dilution was applied on the sand. Twenty worker termites (*Coptotermes formosanus*) were released there just after the application or after keeping at 40° C. for a designated time. Mortality was observed 48 hours after releasing. The test was repeated twice and calculated the average. The result is given in Table 1.

TABLE 1

| Samples | Dilution rate | Mortality (%) | | |
|---|---|---|---|---|
| | | Immediately after application | After 2 months | After 4 months |
| Ex. 1 | ×100 | 100 | 100 | 88 |
| Ex. 2 | ×100 | 100 | 100 | 93 |
| Ref. Ex. 1 | ×100 | 100 | 60 | 33 |

Test Example 2

Each formulation obtained in Examples 1-2 and Reference example 1 was diluted with ion-exchange water to a designated concentration, and 0.54 ml of the dilution was applied on a glass plate (9 cm×12 cm). Five female and five male cockroaches (*Blattella germanica*) were released there just after the application or after keeping at 25° C. for a designated time. After 48 hours, the mortality of the cockroaches was observed. The test was repeated twice and calculated the average. The result is given in Table 2.

TABLE 2

| Samples | Dilution rate | Mortality (%) | | |
|---|---|---|---|---|
| | | Immediately after application | After 10 days | After 30 days |
| Ex. 1 | ×100 | 100 | 100 | 50 |
| Ex. 2 | ×100 | 100 | 100 | 60 |
| Ref. Ex. 1 | ×100 | 100 | 80 | 0 |

What is claimed is:

1. A microcapsule comprising a core material containing pyrethrin and a capsule shell wall which surrounds said core material,
   wherein the shell wall material comprises gelatin, gum arabic and pectin,
   the core material comprises pyrethrin, a plant oil and a solid substance, and
   the solid substance is clay, talc, amorphous silicon oxide or zinc oxide.

2. A microcapsule obtained by a process comprising the steps of:
   mixing or dissolving gelatin, gum arabic and pectin in alkali water at 30 to 70° C.;
   adding pyrethrin or its solution under pH 5 or more and keeping at 30 to 70° C.;
   adding clay, talc, amorphous silicon oxide or zinc oxide;
   adjusting the pH of the mixture to less than 5 by adding acid and cooling with ice-water; and
   warming to 30 to 70° C. and adding a hardening.

3. The microcapsule according to claim 2, wherein the hardening is calcium chloride.

* * * * *